United States Patent
Maianti et al.

(10) Patent No.: US 7,029,245 B2
(45) Date of Patent: Apr. 18, 2006

(54) BLOOD PUMPING UNIT, WITH A COPLANAR DISK INLET VALVE AND AN ANNULAR OUTLET VALVE

(75) Inventors: Edgardo Costa Maianti, Mirandola (IT); Nicola Ghelli, San Pietro in Casale (IT); Ivo Panzani, Mirandola (IT)

(73) Assignee: Sorin Group Italia S.r.l., Mirandola (IT)

( * ) Notice: Subject to any disclaimer, the term of this patent is extended or adjusted under 35 U.S.C. 154(b) by 204 days.

(21) Appl. No.: 10/430,894

(22) Filed: May 6, 2003

(65) Prior Publication Data

US 2004/0001766 A1    Jan. 1, 2004

(30) Foreign Application Priority Data

May 14, 2002    (IT) ........................... MI2002A1028

(51) Int. Cl.
   *F04B 43/06*    (2006.01)

(52) U.S. Cl. ...................... 417/395; 417/567; 417/566; 137/512; 604/153; 604/154

(58) Field of Classification Search ................ 417/395, 417/567, 566, 313; 137/512; 261/DIG. 28; 604/153, 154
See application file for complete search history.

(56) References Cited

U.S. PATENT DOCUMENTS 1,334,507 A * 3/1920 Shartle ........................ 417/567
1,628,096 A * 5/1927 Worth ......................... 417/458
2,455,480 A 12/1948 Hadley (Continued)

FOREIGN PATENT DOCUMENTS

EP    0 724 889 A2    8/1996

(Continued)

OTHER PUBLICATIONS

Belenger, J. and Knight, C.J., "Matching Between ECC Requirements and New Pump Design", in Thirty Years of Extracorporeal Circulation, Edts. Hagl S., Klovekorn, W.P., Mayr N., Sebening, F., Deutsches Herzzentrum Munchen, pp. 421-426, 1984.

(Continued)

*Primary Examiner*—Timothy S. Thorpe
*Assistant Examiner*—Emmanuel Sayoc
(74) *Attorney, Agent, or Firm*—Popovich, Wiles & O'Connell, P.A.

(57) ABSTRACT

A unit for pumping fluid, particularly blood, is provided with an enclosure that has two half-shells and an elastic membrane fixed perimetrically to the enclosure in order to divide its space into two parts. One of the half-shells is provided with valves that are located at the opening of two connecting ducts for the intake and delivery of the fluid, and the other half-shell is connected to a line of working fluid that is alternately pressurized and depressurized. The first valve is a disk-shaped sheet made of elastic material. The first valve is in a central position with a support that is fixed to the opening of the first duct for connection to the outside and is suitable to rest at its peripheral region on the support. A second valve is a sheet of elastic material located at the peripheral region of the disk at the opening of the second duct for connection to the outside which lies at the peripheral region of the opening of the first duct.

20 Claims, 7 Drawing Sheets

U.S. PATENT DOCUMENTS

| | | | |
|---|---|---|---|
| 3,039,399 A | | 6/1962 | Everett |
| 3,148,624 A | | 9/1964 | Baldwin |
| 3,298,320 A | | 1/1967 | Latham |
| 3,314,600 A | * | 4/1967 | Hadley .................... 417/566 |
| 3,508,848 A | * | 4/1970 | Schmidlin ................ 417/395 |
| 3,955,557 A | | 5/1976 | Takagi |
| 4,084,606 A | | 4/1978 | Mittleman |
| 4,360,324 A | * | 11/1982 | Ohara et al. ............. 417/388 |
| 4,385,869 A | * | 5/1983 | Omata ..................... 417/271 |
| 4,411,603 A | * | 10/1983 | Kell ........................ 417/479 |
| 4,468,177 A | | 8/1984 | Strimling |
| 4,634,651 A | * | 1/1987 | Okawara et al. .......... 430/114 |
| 4,687,423 A | * | 8/1987 | Maget et al. ............. 417/379 |
| 5,201,643 A | * | 4/1993 | Hirosawa et al. ......... 417/472 |
| 5,270,005 A | | 12/1993 | Raible |
| 5,704,520 A | * | 1/1998 | Gross ...................... 222/334 |
| 5,728,069 A | | 3/1998 | Montevecchi et al. |
| 6,428,747 B1 | * | 8/2002 | Dueri et al. ............... 422/46 |
| 6,435,844 B1 | * | 8/2002 | Fukami .................... 417/395 |
| 6,468,056 B1 | * | 10/2002 | Murakoshi ................ 417/395 |
| 2001/0038796 A1 | * | 11/2001 | Schluecker ............... 417/383 |

FOREIGN PATENT DOCUMENTS

| | | |
|---|---|---|
| EP | 0 724 889 A3 | 9/1997 |
| EP | 1 180 375 A1 | 2/2002 |

OTHER PUBLICATIONS

Ducko, C.T., et al., "The Effect of Valve Type and Drive Line dP/dt on Hemolysis in the Pneumatic Ventricular Assist Device", *Art. Organs*, 18(6), pp. 454-460, 1994.

Hubbard, L.C., et al., "Spallation Using Roller Pumps and its Clinical Implications", *AmSect Proceedings III*, 27, 1975.

Jacobs, L.A., et al., "Improved Organ Function During Cardiac Bypass with a Roller Pump Modified to Delivery Pulsatile Flow", *J. Thorac. Cardio. Vasc. Surg.*, 58 pp. 707, 1969.

Kletschka, H.D., et al., "Artificial Heart: Development of Efficient Atraumatic Blood Pump. A Review of the Literature Concerning In Vitro Testing of Blood Pumps for Hemolysis", *Minn. Med.*, 58, 756-781, (Oct. 1975).

Koller, T. and Hawrylenko, A., "Contribution in the In Vitro Testing of Pumps for Extracorporeal Circulation", *J. Thorac. Cardiovasc. Surg.*, 54, pp. 22-29, 1967.

European Search Report for counterpart Application No. 03009794.3 (3 pages).

* cited by examiner

BLOOD PUMPING UNIT, WITH A COPLANAR DISK INLET VALVE AND AN ANNULAR OUTLET VALVE

FIELD OF THE INVENTION

The present invention relates to a unit for pumping fluid, particularly blood.

BACKGROUND OF THE INVENTION

It is known that during many operations it is necessary to provide an extracorporeal circulation of blood in a circuit which includes a pump. One type of pump suitable for use in such extracorporeal circuits is a pulsating pump. The pulsating pump includes an enclosure suitable to contain a portion of space in which there acts an elastic membrane or diaphragm. The diaphragm is actuated by a working fluid acting against one face of the membrane which is alternatively pressurized and depressurized according to the heart rate and provides at the other face the suction and delivery of the blood.

Known pulsating pumps are not entirely satisfactory, particularly with respect to the valves that regulate the inflow and outflow of the fluid.

SUMMARY OF THE INVENTION

The aim of the present invention is to provide a pumping unit that has maximum constructive simplicity, so as to ensure modest costs and great reliability in operation. Within the scope of this aim, an object of the invention is to provide a pumping unit that is very compact and is suitable to be integrated easily with other devices that are present in the extracorporeal circuit through which the blood is meant to flow, such as for example a heat exchanger or an oxygenation apparatus.

The proposed aim and object are achieved by a unit for pumping fluid, particularly blood, according to the invention, which is provided with an enclosure that comprises two half-shells that are suitable to define internally a portion of space or pumping chamber, which contains an elastic membrane or diaphragm, which is fixed around the perimeter to the enclosure and lies within the portion of space, dividing it into two half-shell shaped parts. One of the half-shells being provided with valves that are located at the opening of two ducts for the connection of the portion of space defined by the enclosure to the outside for the intake and delivery of the fluid, the other half-shell being connected to a line of working fluid that is alternately pressurized and depressurized. The pumping unit includes a first valve that comprises a disk-shaped sheet made of elastic material, which is associated in a central position with a support that is fixed to the opening of the first duct for connection to the outside and is suitable to rest at its peripheral region on the support. A second valve comprises a sheet made of elastic material, which is located at the peripheral region of said disk at the opening of a second of the two ducts for connection to the outside which lies at the peripheral region of the opening of the first duct, which is fixed at one of its edges and is suitable to rest on the opening at the other edge.

BRIEF DESCRIPTION OF THE DRAWINGS

Further characteristics and advantages will become better apparent from the description of some preferred but not exclusive embodiments of the invention, illustrated only by way of non-limiting examples in the accompanying drawings, wherein.

DETAILED DESCRIPTION OF THE PREFERRED EMBODIMENTS

Figure 1:
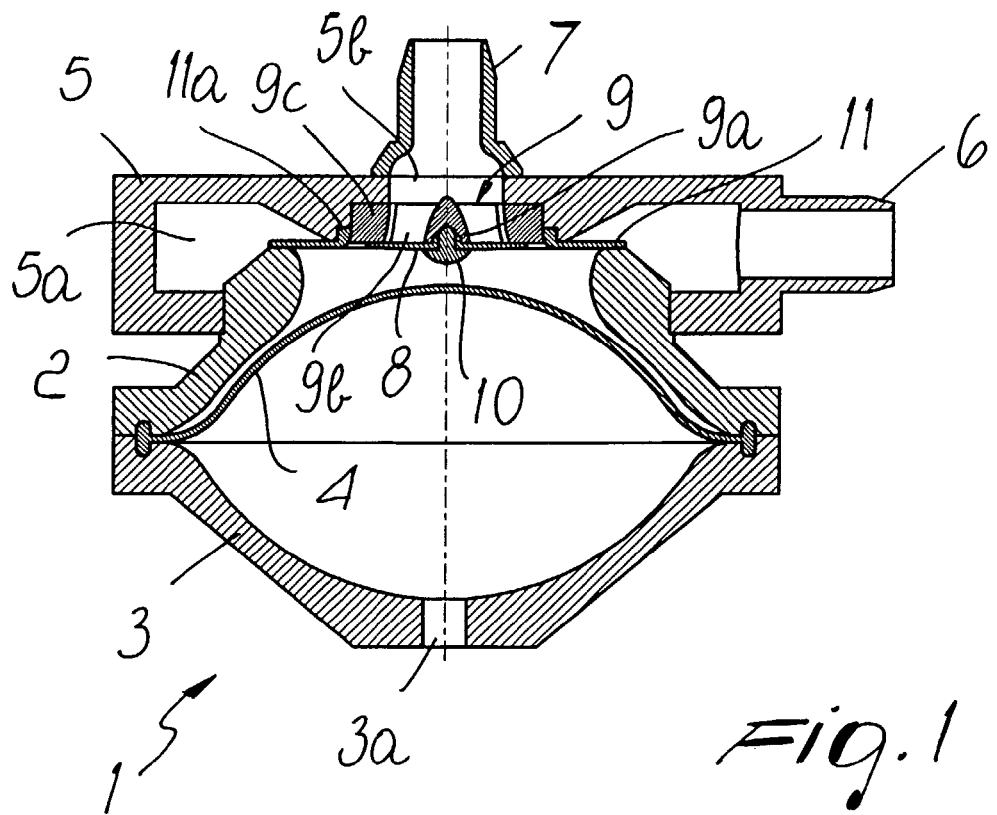
FIG. 1 is a sectional view of the pumping unit of the invention at rest.

With reference to FIGS. 1 to 4, the numeral 1 generally designates the pumping unit provided with a body portion or enclosure that comprises two portions including a half-shell 2 and a second half-shell 3. The two half-shell portions define a pumping chamber 25 comprising an internal portion of space in which the elastic membrane or diaphragm 4 is arranged, dividing the space into two parts. The membrane is fixed around its perimeter at the joining plane of the two half-shells, which are rigidly connected by means of a film of adhesive.

The lower half-shell 3 is provided with a fluid port comprising hole 3a for connection to a line of working fluid, such as air, which is alternatively pressurized and depressurized. The frequency of the alternation of pressure and vacuum determines the rate at which fluid is pumped through the unit and may advantageously be selected to substantially coincide with the heart rate.

A discharge portion comprising ring 5 is monolithically applied to the upper half-shell 2 and is provided with circumferential cavity 5a, having an outlet duct fluidly connected to outlet connector 6. This connector is suitable to be connected to a line for the delivery of the fluid, particularly blood. Ring 5 is also provided with an inlet duct 5b for connection to an inlet connector 7, which is fixed by means of a film of adhesive and is suitable to be connected to a fluid intake line.

An inlet valve is provided at the opening of the duct 5b and comprises a generally circumferential disk 8 made of elastic material, located centrally about an inlet valve support 9. Support 9 is fixed to the opening of the duct 5b. More specifically, disk 8 is fixed by means of a stud 10 to a central hub 9a of inlet valve support 9, which is connected by means of wings 9b to an outer body 9c of support 9. Disk 8 has an outer peripheral portion 8a which seals against outer body 9c when the inlet valve is closed as in FIG. 1. When the inlet valve is in the open position as shown in FIG. 3, portion 8a is moved away from outer body 9c to allow fluid flow through outer body 9c through openings between wings 9b.

The opening of outlet connector 6 is located at the peripheral region of the opening of the inlet duct 5b and gives access to the circumferential cavity 5a. The access to the circumferential cavity 5a is controlled by an outlet valve that comprises an annular sheet of elastic material 11, which is fixed at its inner edge 11a between ring 5 and outber body 9c. An outer edge 11b rests on half-shell 2 when the valve is in the closed position as shown in FIG. 3.

The operation of the invention is illustrated by the Figures.

Figure 3:
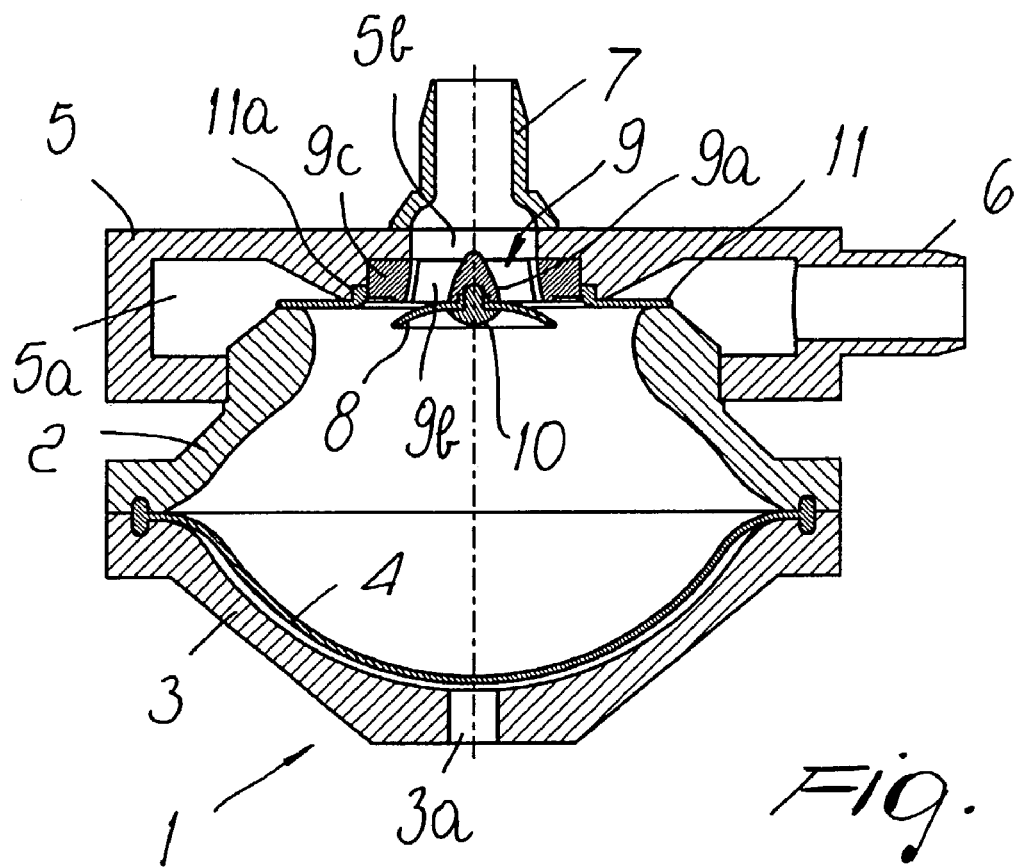
FIGS. 3 and 4 are sectional views of the pumping unit respectively during intake and during delivery of the fluid.

From the inactive position shown in FIG. 1, a negative pressure of the working fluid below the membrane 4 moves membrane 4 downward, as shown in FIG. 3. This movement causes a suction between wings 9b, opening the inlet valve by causing an outer peripheral edge of disk 8 to descend as shown in FIG. 3. This in turn causes the pumping chamber 25 to be filled by the fluid.

During this intake step, annular sheet 11 remains in the position for blocking the flow of fluid into the circumferential cavity 5a or outlet connector 66.

Figure 4:
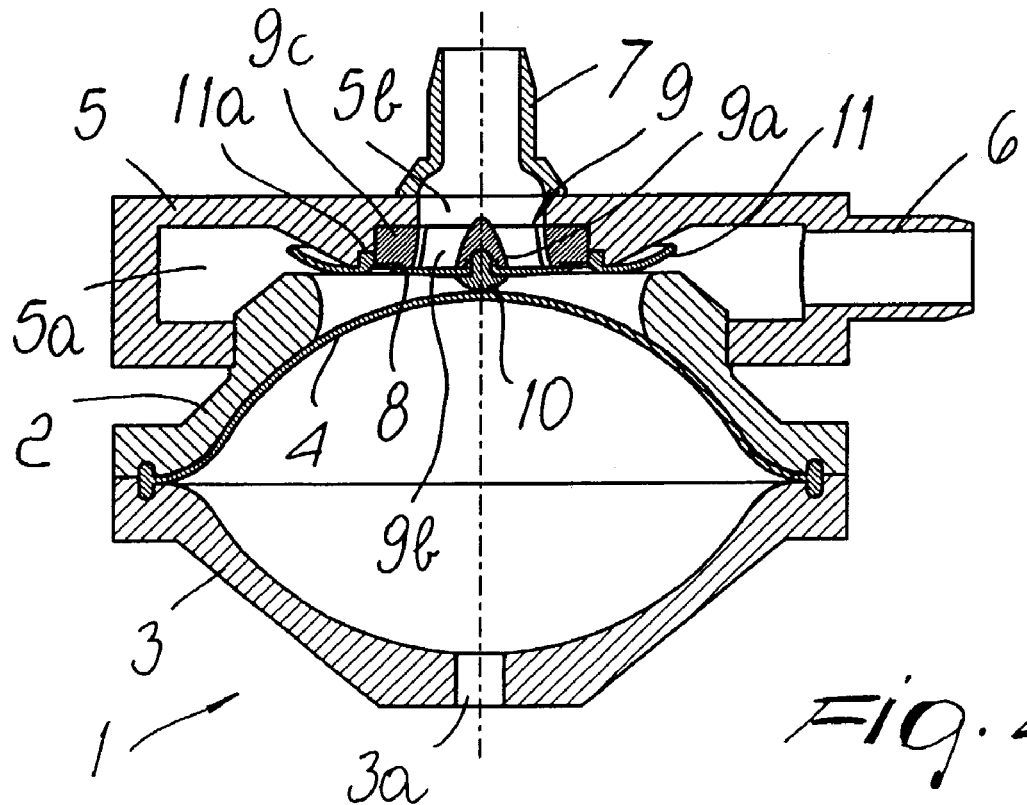

The intake step is followed by a delivery step. During the delivery step, the working fluid is pressurized resulting in movement of membrane 4 to the position shown in FIG. 4. This movement pressurizes the pumping chamber, closing the inlet valve and opening the outlet valve. In particular, as seen in FIG. 4, disk 8 of the inlet valve sits against outer body 9c, thus closing the inlet valve, and the outer periphery 11b of sheet 11 moves away from half-shell 2, thus opening the outlet valve. The opening of the outlet valve allows the fluid, particularly blood, to access the circumferential cavity 5a and from there the delivery connector 6.

Figure 5:
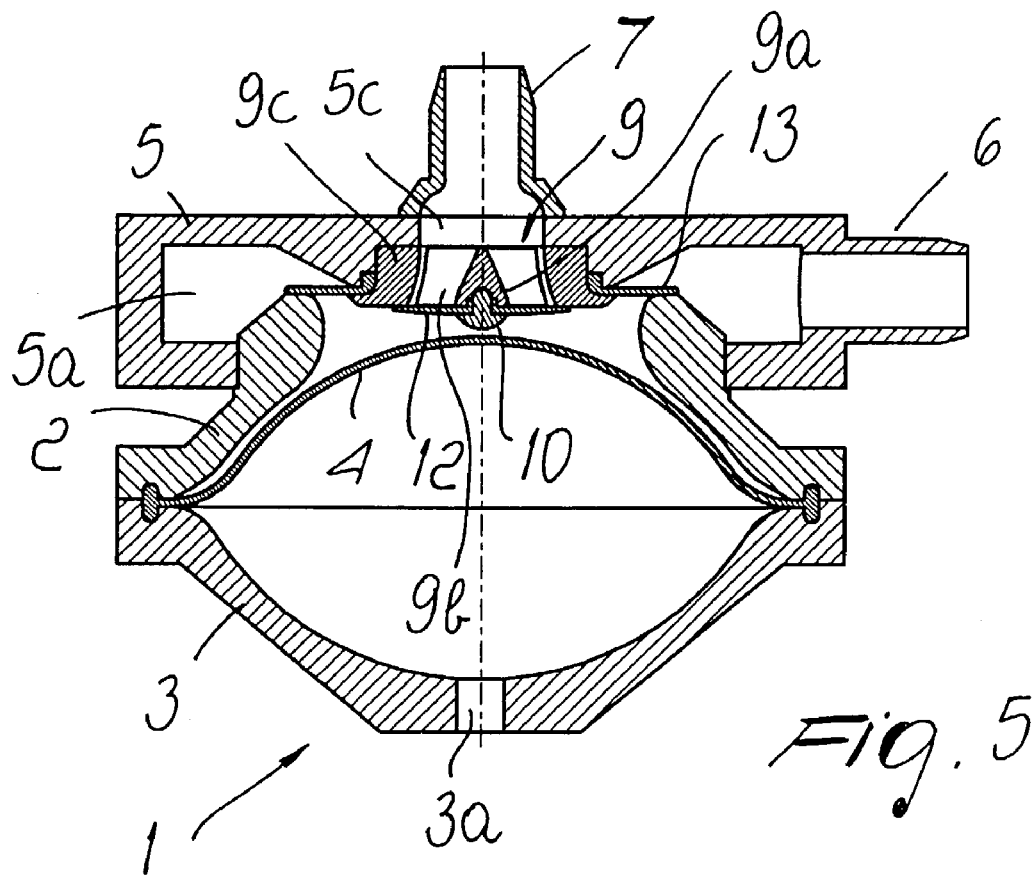
FIGS. 5 and 6 are sectional views of two variations of the invention.

FIG. 5 is a view of another embodiment of of the invention. This embodiment is similar to that illustrated in FIG. 1, where elastic disc 8 is coplanar with elastic sheet 11. Here, disk 12 of the inlet valve and annular sheet 13 of the outlet valve are arranged on parallel planes, with disk 12 below annular sheet 13. That is, disk 12 is closer to the center of the portion of space formed by the enclosure than is annular sheet 13.

Figure 6:
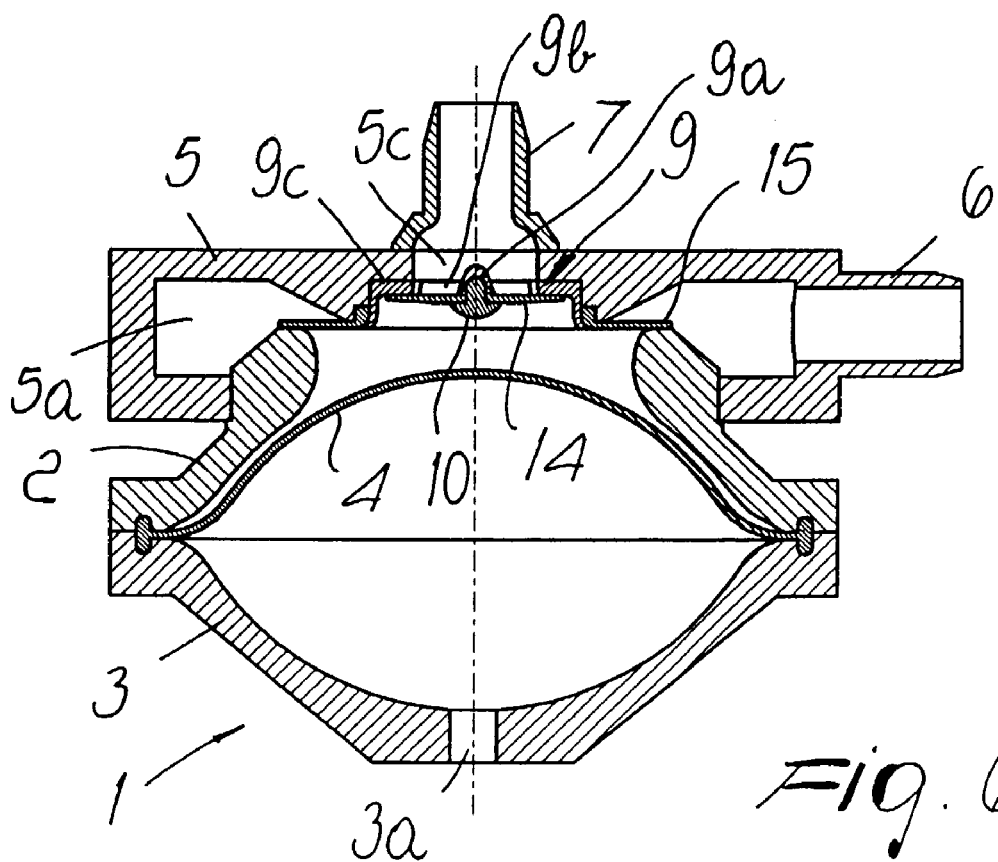

The opposite situation occurs in the embodiment shown in FIG. 6, in which annular sheet 15 and disk 14 are arranged on parallel planes, but the annular sheet 15 is closer to the center than disk 14. In every other respect, the two embodiments shown in FIGS. 5 and 6 are similar to the first described embodiment.

Figure 7:
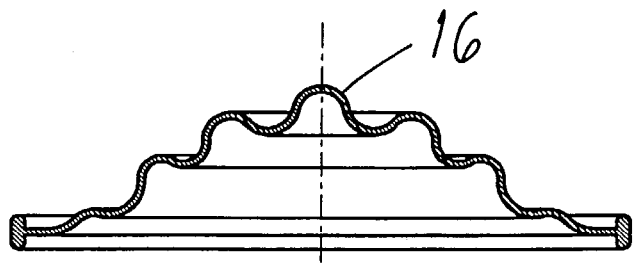
FIG. 7 is a sectional view of a variation of the elastic membrane or diaphragm shown in FIG. 1.
Figure 2:
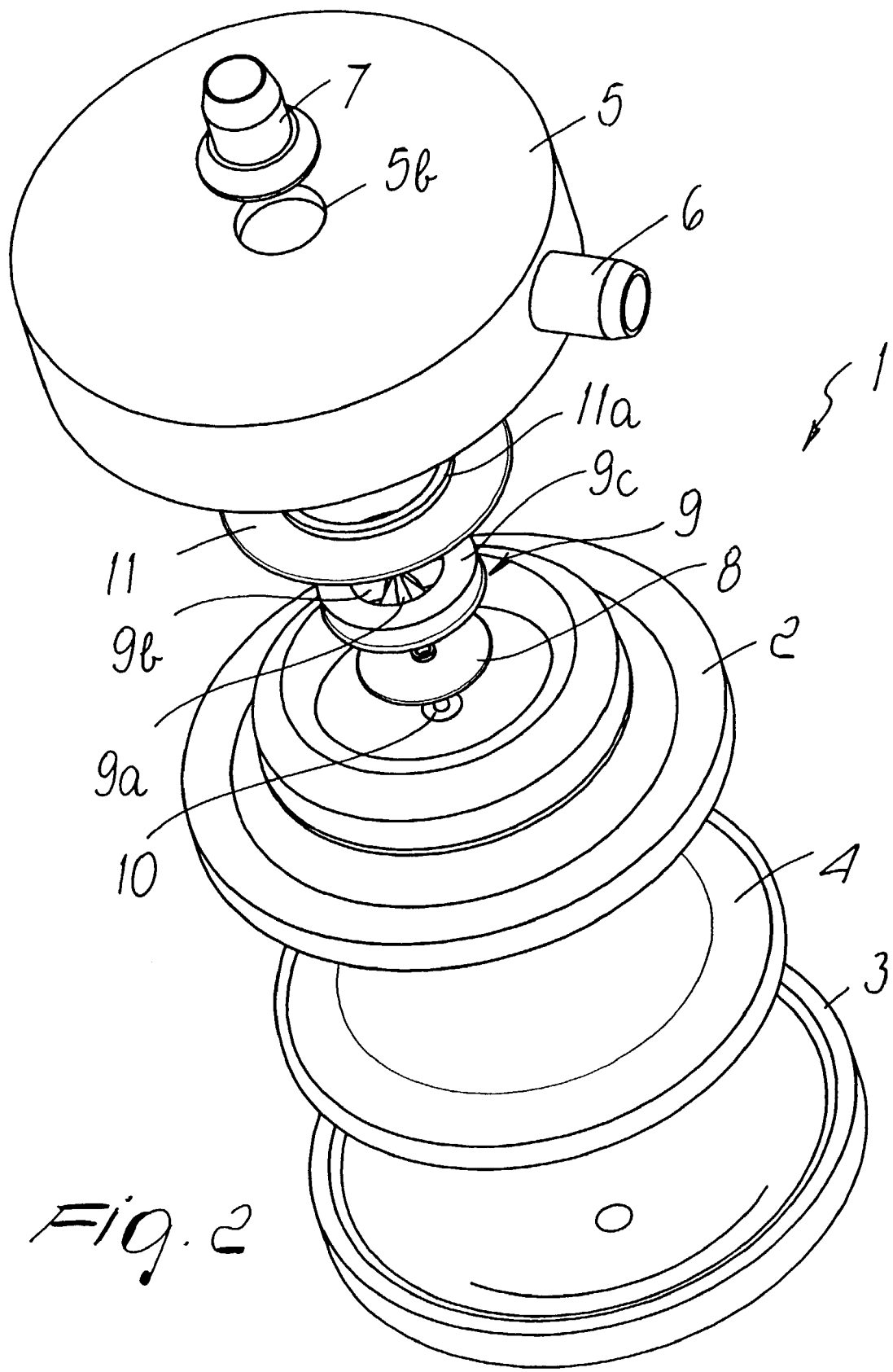
FIG. 2 is an exploded view of the pumping unit of the invention.

FIG. 7 illustrates another embodiment of an elastic membrane or diaphragm. FIG. 7 shows elastic membrane 16, which is similar in function to elastic membrane 4 of FIGS. 1 to 6. However, instead of being smooth as shown in previous embodiments, membrane 16 is corrugated in order to improve its flexibility characteristics.

Figure 8:
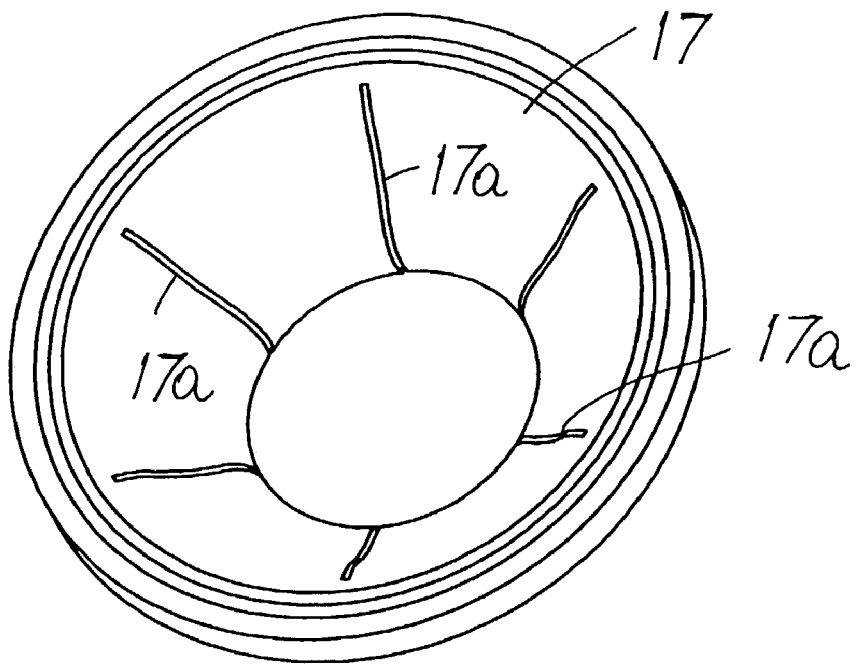
FIG. 8 is a perspective view of the internal surfaces of the two half-shells of the enclosure of one embodiment of this invention.
Figure 8:
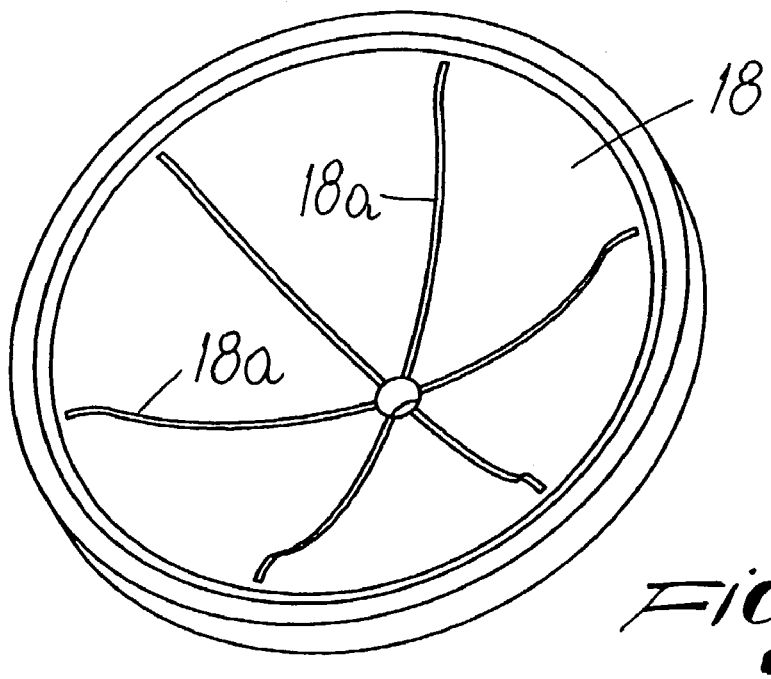

FIG. 8 is a view of the internal surface of two half-shells 17 and 18, which comprise alternate embodiments of the enclosure of the pumping unit. Instead of being smooth as for the two half-shells 2 and 3 described above, half-shells 17 and 18 have grooves 17a and 18a, respectively, These grooves serve to prevent the elastic membrane 4 from sticking to the surface of a half-shell.

Figure 9:
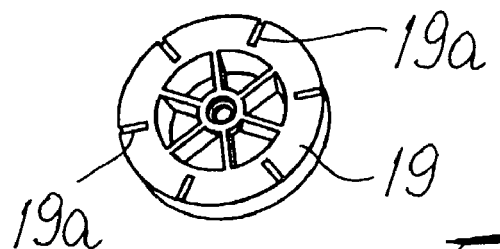
FIG. 9 is a perspective view of the support of the inlet valve of one embodiment of this invention.

For the same purpose, support 19, shown in FIG. 9, of the inlet valve is provided with grooves 19a at the surface directed toward membrane 4. As an alternative to grooves 17a, 18a and 19a, slightly protruding teeth or ridges might be present on the respective surfaces.

Figure 11:
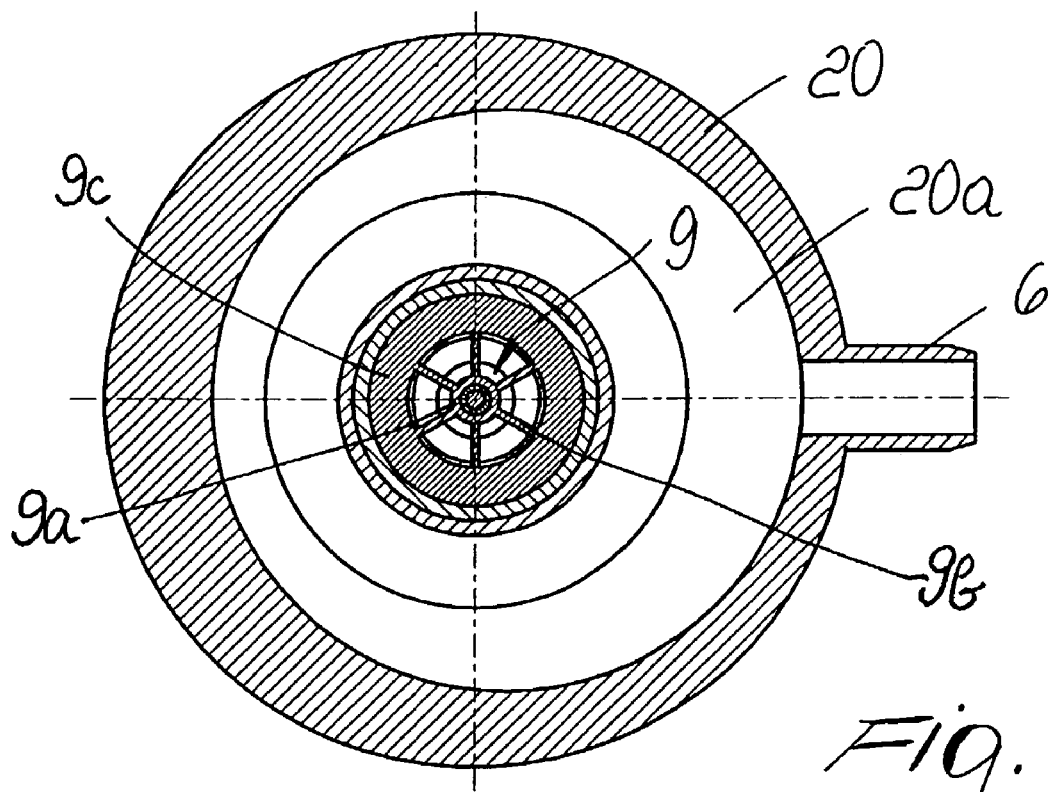
FIG. 11 is a sectional view of an embodiment of this invention, taken along line XI–XI of FIG. 10.
Figure 10:
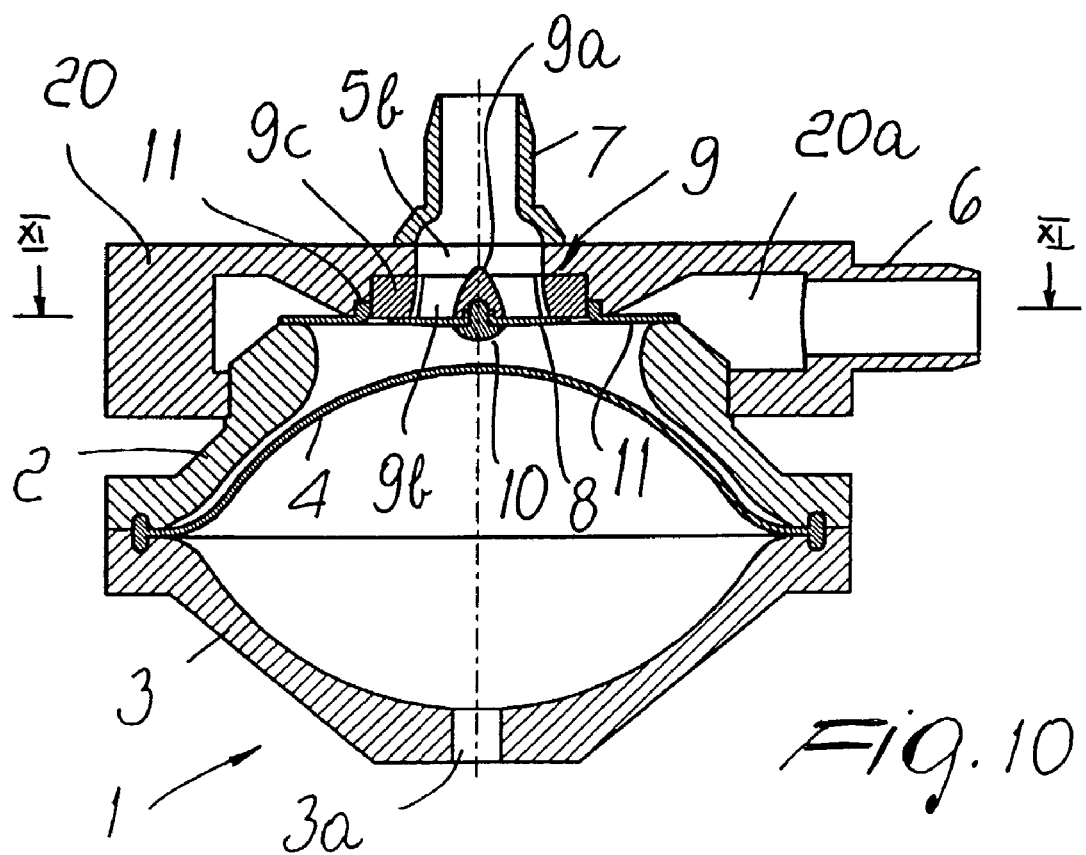
FIG. 10 is a sectional view of an embodiment of this invention.

An improvement to the fluid-dynamics characteristics at the delivery can be achieved by arranging, as shown in FIGS. 10 and 11, ring 20 provided with a circumferential cavity 20a eccentrically with respect to the opening of the delivery duct instead of coaxially thereto, as occurs in the embodiment shown in FIG. 1.

Figure 12:
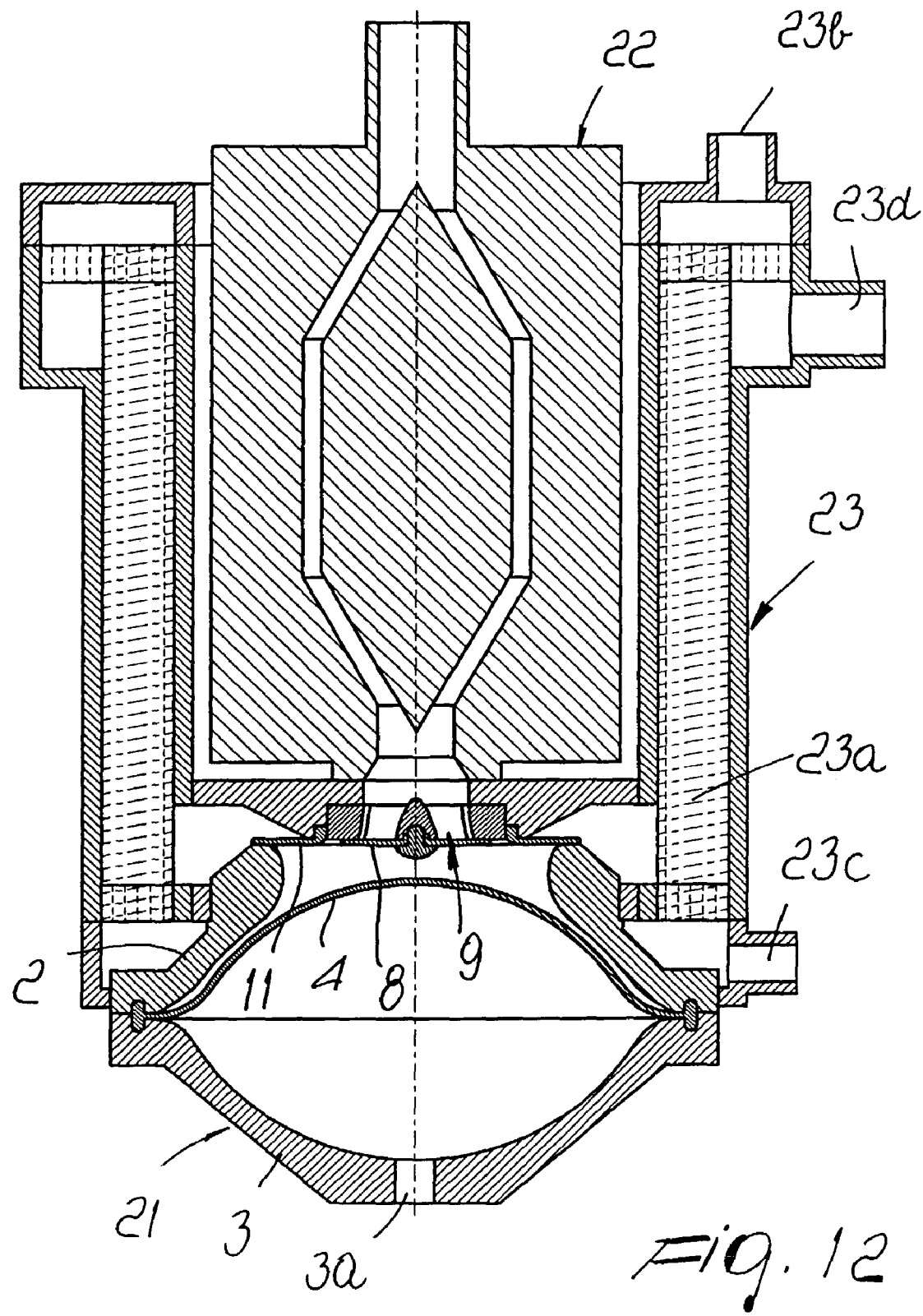
FIG. 12 is a sectional view of the pumping unit integrated in an assembly with an oxygenation apparatus and a heat exchanger.

FIG. 12 illustrates the compactness and synergy provided in the coupling of a pumping unit 21 according to the invention to other devices comprised within a circuit for the extracorporeal circulation of blood, such as the heat exchanger 22, connected directly to the inlet connector, and the oxygenation apparatus 23, in which the blood from the pumping unit 21 enters directly into an oxygenation chamber 23a containing hollow fibers, through which oxygen flows by entering through port 23b and exiting through port 23c. The blood travels upwardly through the oxygenation chamber contacting the exterior of the fibers and then exits the oxygenator through connector 23d.

The described invention is susceptible of numerous other modifications and variations, all of which are within the scope of the inventive concept. Thus, for example, the duct whose opening is controlled by the valve that comprises the disk made of elastic material can be connected to the fluid delivery line, while the sheet of elastic material arranged in the peripheral region of said disk, comprised in the other valve, can control the opening of the duct connected to the intake line, and in this case can be fixed at the outer edge.

What is claimed is:

1. A device for pulsed pumping of blood, comprising:
 a body portion;
 a pumping chamber disposed within the body portion having a diaphragm, an inlet duct and an outlet duct;
 an inlet valve support fixed to an opening in the inlet duct;
 an inlet disk valve attached to the inlet valve support for controlling flow of blood from the inlet duct into the pumping chamber; and
 an annular outlet valve for controlling flow of blood from the pumping chamber to the outlet duct,
 wherein the inlet valve and the outlet valve both comprise a planar elastic material and wherein the inlet valve and the outlet valve are coplanar.

2. The device of claim 1 wherein the diaphragm is moved from a first position to a second position by dynamic pressure created by a working fluid.

3. The device of claim 1 wherein the body portion includes an upper portion and a lower portion.

4. The device of claim 3 wherein the inlet duct and the outlet duct are in the upper portion.

5. The device of claim 3 wherein the lower portion includes a fluid port in communication with a working fluid that acts on the diaphragm to alternately pressurize and depressurize the pumping chamber.

6. The device of claim 3 further having a circumferential ring attached to the upper portion, the circumferential ring having a circumferential cavity connected to receive blood from the inlet duct.

7. The device of claim 6 wherein the circumferential ring is eccentric to the inlet duct.

8. The device of claim 6 wherein the circumferential ring is coaxial to the inlet duct.

9. The device of claim 1 further comprising an oxygenation chamber in fluid communication with the outlet duct.

10. The device of claim 1 further comprising a heat exchanger in fluid communication with the inlet duct.

11. A device for pulsed pumping of blood, comprising:
 a body portion having an upper portion and a lower portion;
 a pumping chamber defined by the upper portion and the lower portion, and having a diaphragm an inlet duct and an outlet duct, at least the inlet duct attached to the upper body portion;

an inlet valve support fixed to an opening in the inlet duct;

an inlet valve attached to the inlet valve support for controlling flow of blood from the inlet duct into the pumping chamber;

an outlet valve for controlling the flow of blood from the pumping chamber to the outlet duct; and a circumferential ring attached to the upper portion, the circumferential ring having a circumferential cavity connected to receive blood from the inlet duct, wherein the inlet valve and the outlet valve both comprise a planar elastic material and wherein the inlet valve and the outlet valve are coplanar.

12. The device of claim 11 wherein the outlet valve is an annular valve.

13. The device of claim 11 wherein the inlet valve is a disk valve.

14. The device of claim 11 wherein the diaphragm is moved from a first position to a second position by dynamic pressure created by a working fluid.

15. The device of claim 11 wherein the inlet duct and the outlet duct are in the upper portion.

16. The device of claim 11 wherein the lower portion includes a fluid port in communication with a working fluid that acts on the diaphragm to alternately pressurize and depressurize the pumping chamber.

17. The device of claim 11 wherein the circumferential ring is eccentric to the inlet duct.

18. The device of claim 11 wherein the circumferential ring is coaxial to the inlet duct.

19. The device of claim 11 further comprising an oxygenation chamber in fluid communication with the outlet duct.

20. The device of claim 11 further comprising a heat exchanger in fluid communication with the inlet duct.

* * * * *